United States Patent [19]
Prevey, III et al.

[11] Patent Number: 5,737,385
[45] Date of Patent: Apr. 7, 1998

[54] AUTOMATED SYSTEM FOR USE IN THE DETERMINATION OF SUBSURFACE MATERIAL PROPERTIES BY X-RAY DIFFRACTION

[75] Inventors: Paul S. Prevey, III; Glenn A. Plunkett, both of Cincinnati, Ohio

[73] Assignee: Lambda Research, Inc., Cincinnati, Ohio

[21] Appl. No.: 674,434

[22] Filed: Jul. 2, 1996

[51] Int. Cl.[6] ................................................. G01N 23/20
[52] U.S. Cl. .............................. 378/71; 378/73; 378/79
[58] Field of Search ........................ 378/71, 73, 79, 378/81

[56] References Cited

U.S. PATENT DOCUMENTS

4,709,383  11/1987  Goto et al. ............................ 378/71 .

Primary Examiner—Craig E. Church
Attorney, Agent, or Firm—Mark F. Smith

[57] ABSTRACT

The present invention is directed to an automated system for use in the determination of subsurface material properties of a specimen by X-ray diffraction, comprising a specimen support, a rotatable mounting and aligning fixture for mounting the specimen support onto the shaft of a motor driven positioning system, a chemical holding tank having a first half section having a chemical holding chamber for providing a chemical bath for removing surface material from the specimen and a second half section for providing a position for permitting X-ray diffraction measurement of the specimen, a chemical reservoir in fluid communication with the chemical holding chamber of chemical holding tank to provide a steady supply of chemical solution to the chemical holding chamber through a closed loop system, a neutralization tank for receiving contaminated rinse water from the chemical holding tank, and an electronic controller for controlling the cycling of the specimen between the chemical holding chamber and the position for receiving a beam of X-rays from an X-ray source.

28 Claims, 7 Drawing Sheets

AUTOMATED SYSTEM FOR USE IN THE DETERMINATION OF SUBSURFACE MATERIAL PROPERTIES BY X-RAY DIFFRACTION

BACKGROUND OF THE INVENTION

This invention relates to X-ray diffraction, and more particularly, to an automated system for use in the determination of subsurface material properties by X-ray diffraction.

X-ray diffraction has become a commonly employed tool for analyzing specimens of material for determining the chemical composition, the residual stress, the phase composition, the microstructural characteristics, and other properties of the material. Various types of apparatus and techniques are known in the prior art for determination of subsurface properties in specimens of material by measurement of variations in X-ray diffraction patterns. Typically, a collimated beam of X-rays from a source is projected, along a plane perpendicular to the surface of a specimen, onto the specimen surface. When the X-ray radiation impinges upon the surface of the specimen, diffracted radiation extends and expands outwardly from the surface and is detected by various detectors positioned at predetermined positions around the specimen. By measuring the angle and intensity of the diffracted X-ray beams and comparing the derived data with diffractograms of known materials and various other conventional means of analyzing data, an analysis of the material comprising the specimen may be made.

The depth of penetration of the X-ray beam is typically shallow, in the order of 5 to 24 μm for most materials. Accordingly, analysis of the material comprising the specimen based on X-ray diffraction techniques is limited to the surface layer of the specimen. In order to analyze the material properties of the specimen below the original surface, surface material must be removed in incremental layers, without affecting the original state of the specimen, and additional X-ray diffraction measurements taken.

Conventional mechanical means of removing surface material, such as grinding or polishing, are not suitable as they may alter the properties of the material by means of plastic deformation or heat. Accordingly, chemical processes, such as passive etching, electropolishing, electrolytic etching, electrochemical machining (ECM), are conventionally employed to remove surface material from the specimen to be analyzed.

Unfortunately, however, until the present invention, the removal of surface material from a specimen to be analyzed using conventional chemical processes required the removal of the specimen from the diffraction apparatus. The specimen must then be manually inserted into a chemical bath and carefully monitored until the proper amount of surface material is removed. In order to analyze the newly exposed surface layer of the specimen, the specimen must be precisely mounted back into position on the diffraction apparatus and additional X-ray diffraction measurements taken.

It should be clear to one skilled in the industry that the prior art techniques and apparatus are time-consuming and labor-intensive and are therefore prohibitively expensive for use in exhaustive studies or high volume or quality control testing. Further, such prior art techniques and apparatus make the handling of large number of samples difficult and introduce the possibility of human error.

Accordingly, a need exists for a method and an apparatus which eliminates the need to manually remove a specimen from a diffraction apparatus for surface layer removal and to manually reinsert the specimen into position on the diffraction apparatus for additional X-ray measurements. Furthermore, a need exists for a method and an apparatus for automatically cycling a specimen through a chemical bath for surface layer removal and back into position for additional X-ray diffraction measurements.

SUMMARY OF THE INVENTION

The present invention is directed to an automated system for use in the determination of subsurface material properties of a specimen by X-ray diffraction, comprising a specimen support, a rotatable mounting and aligning fixture for mounting the specimen support onto the shaft of a motor driven positioning system, a chemical holding tank including a first half section having a chemical holding chamber for providing a chemical bath for removing surface material from the specimen and a second half section for providing a position for permitting X-ray diffraction measurement of the specimen, a chemical reservoir in fluid communication with the chemical holding chamber of the chemical holding tank to provide a steady supply of chemical solution to the chemical holding chamber through a closed loop system, a neutralization tank for receiving contaminated rinse water from the chemical holding tank, and an electronic controller for cooperating with the positioning system to control the cycling of the specimen between the chemical holding chamber and the position for receiving a beam of X-rays from an X-ray source. In operation, the rotatable mounting and aligning fixture is incrementally rotated by the positioning system to automatically cycle the specimen(s) through the chemical bath in the chemical holding chamber for surface layer removal and back into position for X-ray diffraction measurement. The amount of surface material removal is automatically calculated through direct measurement or by calculating the time the sample has been exposed to the chemical solution.

In another preferred embodiment of the invention, the automated system for use in the determination of subsurface material properties of a specimen by X-ray diffraction is adopted for use with a portable diffractometer system. The automated system of the present invention comprises a flexible seal having one end for attaching to the front of a conventional integrated diffractometer system and the other end for attaching to the specimen to form a chemical holding chamber. A chemical solution effective for removing surface material is supplied to the chemical holding chamber from a chemical reservoir through a recirculating closed loop system.

A primary object of this invention, therefore, is to provide an automated system for use in the determination of subsurface material properties of a specimen by X-ray diffraction.

Another primary object of this invention is to provide an automated system for use in the determination of subsurface material properties of a specimen which automatically cycles a specimen through a chemical bath for surface layer removal and back into position for additional X-ray diffraction measurement.

Another primary object of the invention is to provide an automated system for use in the determination of subsurface material properties of a specimen of material by X-ray diffraction which does not require the specimen to be manually removed from the diffraction apparatus for surface layer removal.

Another primary object of the invention is to provide an automated system for use in the determination of subsurface material properties of a specimen by X-ray diffraction which significantly increases the speed of conducting X-ray diffraction studies.

Another primary object of the invention is to provide an automated system for use in the determination of subsurface material properties of a specimen by X-ray diffraction which significantly reduces the cost of conducting X-ray diffraction studies.

These and other objects and advantages of the invention will be apparent from the following description, the accompanying drawings and the appended claims.

DESCRIPTION OF THE PREFERRED EMBODIMENTS

Figure 1:
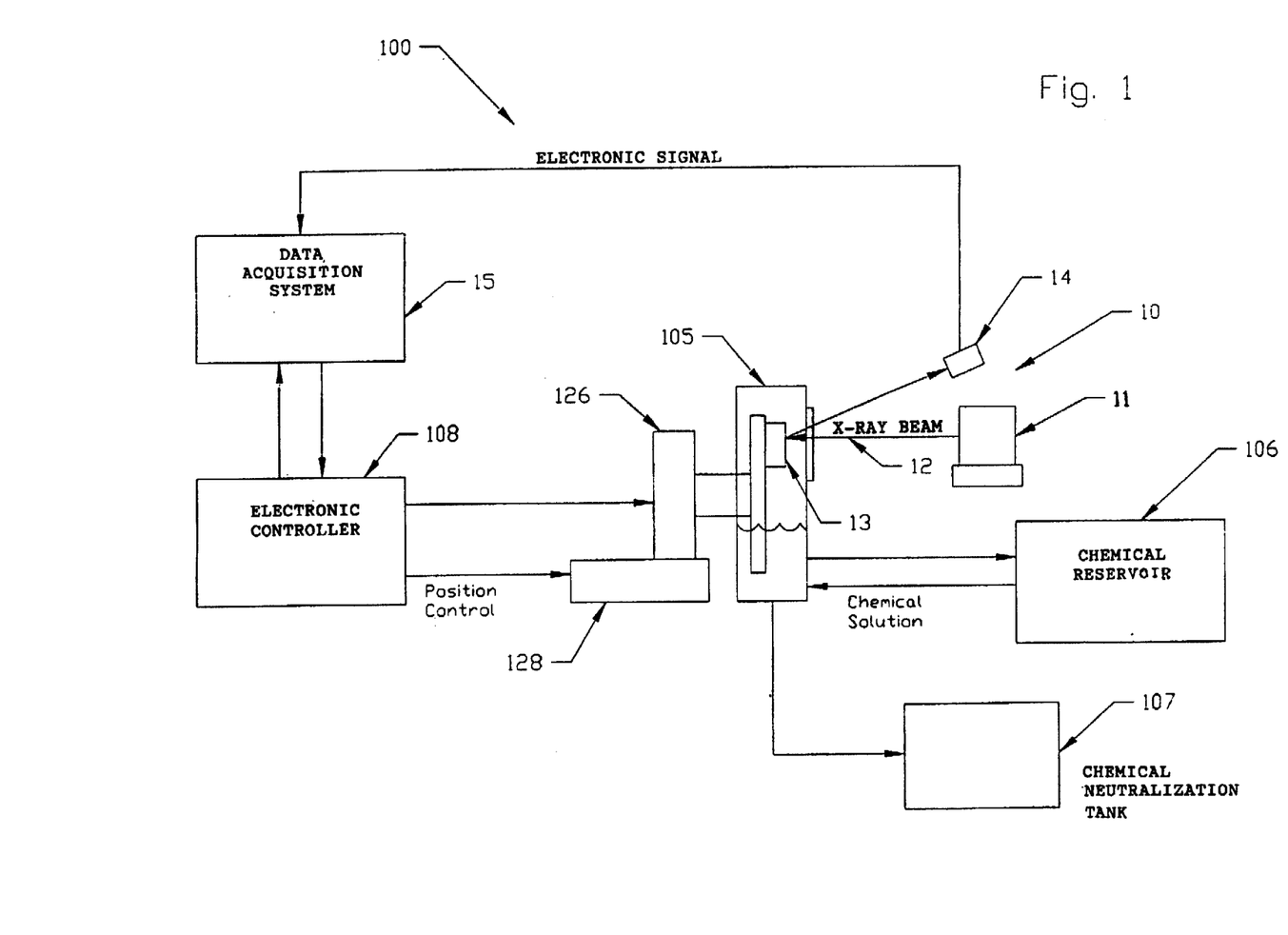
FIG. 1 is a schematic diagram of the automated system for use in the determination of subsurface material properties by X-ray diffraction illustrating the principal of operation of the invention.

The present invention is directed to an automated system for the determination of subsurface material properties of a specimen by X-ray diffraction. Referring to FIG. 1, a conventional X-ray diffraction system, generally designated 10, comprises an X-ray source 11. A collimated beam of X-rays 12 is projected from the X-ray source 11 to the surface of a specimen 13 to be analyzed. At least one X-ray detector 14 intercepts the X-ray beam diffracted from the surface of the specimen 13 and conventionally delivers a signal to a computer controlled data acquisition system 15 for mathematical manipulation.

Figure 2:
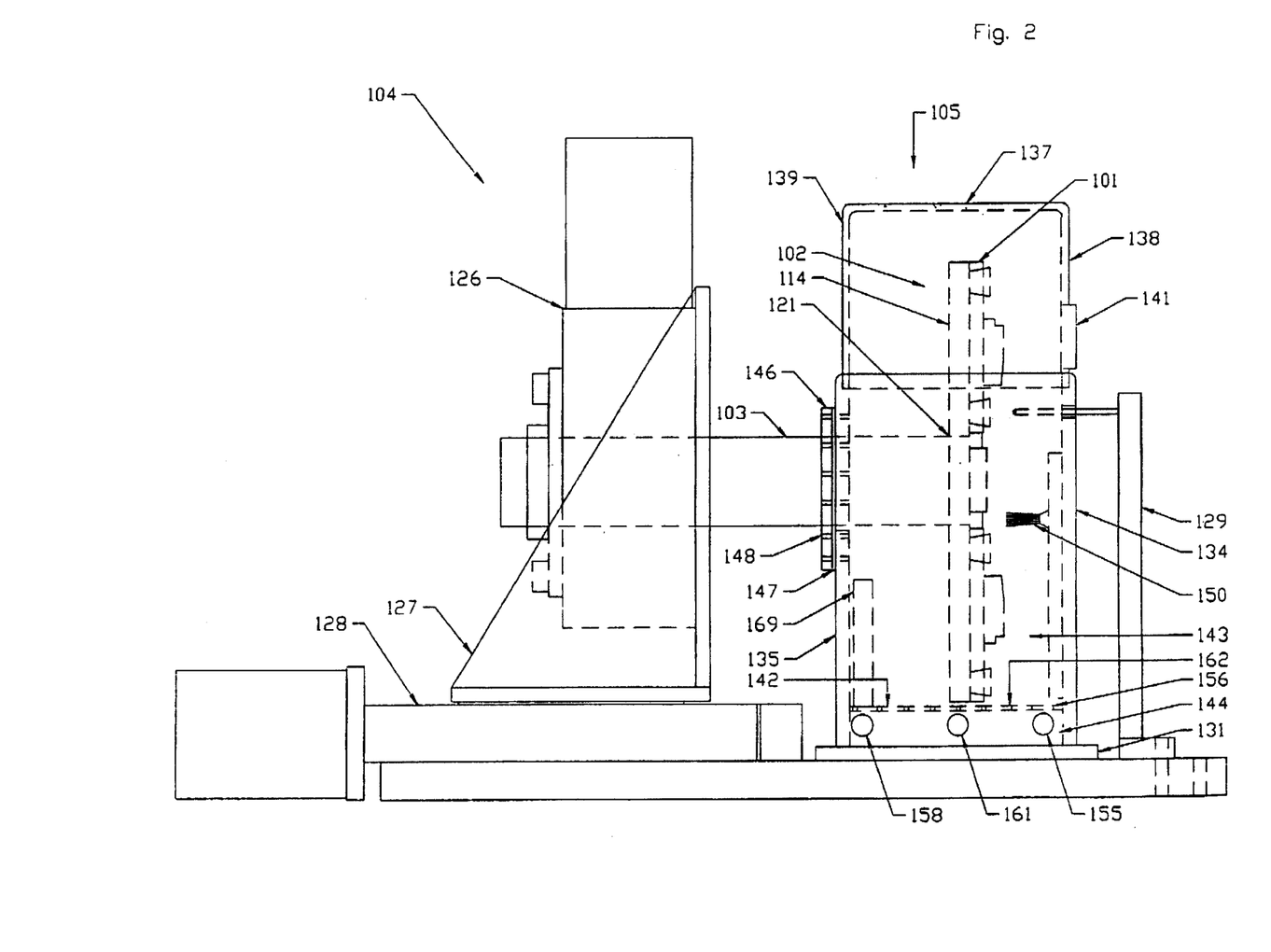
FIG. 2 is a side elevation view of the rotatable mounting and aligning fixture mounted on a drive shaft of a conventional motor driven positioning system.
Figure 3A:
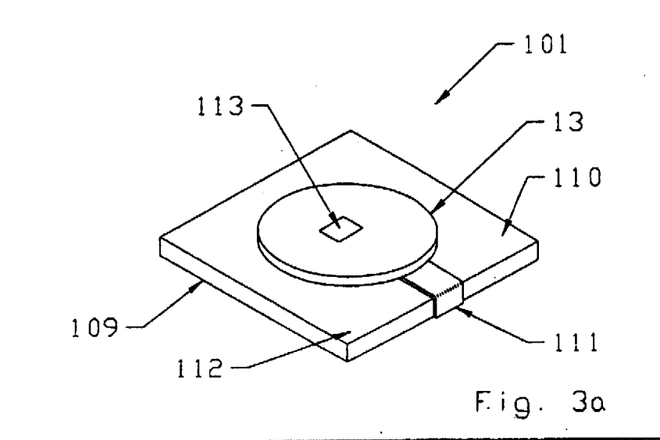
FIGS. 3a through 3d are perspective views of the specimen supporting structure of the present invention showing various shapes and sizes of specimens to be studied.
Figure 3B:
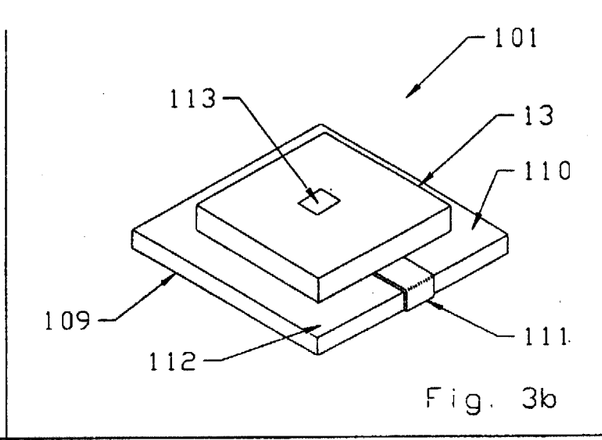
Figure 3C:
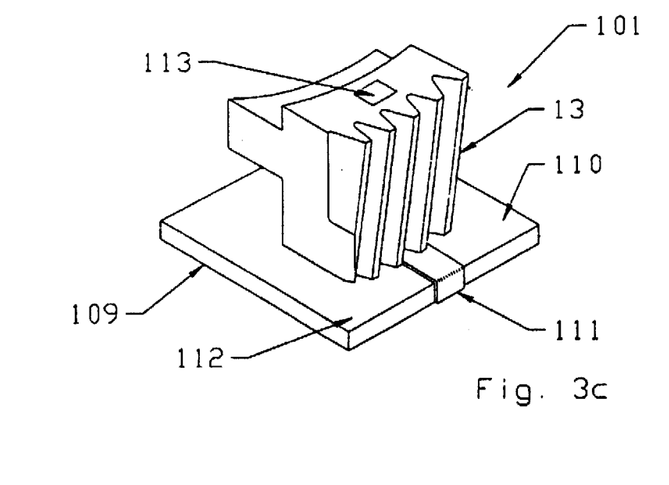
Figure 3D:
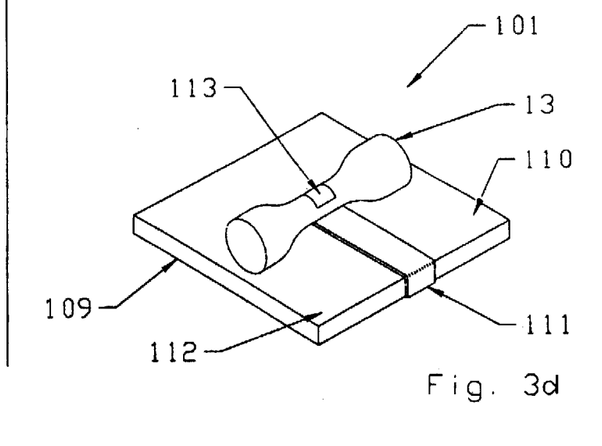

Referring to FIGS. 1 and 2, the automated system for the determination of subsurface material properties by X-ray diffraction of the present invention, generally designated 100, comprises a specimen support 101; a rotatable mounting and aligning fixture 102 for mounting the specimen support 101 onto the rotatable hollow drive shaft 103 of a positioning system 104; a chemical holding tank 105 for providing a chemical bath for removing surface material from a specimen; a chemical reservoir 106 for providing a steady supply of chemical solution to the chemical holding tank 105 through a closed loop system; a chemical neutralization tank 107 for receiving contaminated rinse water from the chemical holding tank 105; and an electronic controller 108 for controlling the cycling of the specimen 13 between the chemical bath contained in the chemical holding tank 105 and a position for receiving a beam of X-rays 12 from the X-ray source 11.

Referring to FIGS. 3a through 3d, the specimen support 101 comprises a chemically inert substrate 109, such as glass, having a planar surface 110 for mounting and supporting a specimen 13 to be analyzed. Preferably, the specimen 13 is bonded to the planar surface 110 of the substrate 109 by an adhesive. However, mechanical attachments or suction devices or other such methods may also be used to mount the specimen 13 on the substrate 109. In the event removal of surface material is to be performed utilizing electrochemical processes, a metal strip 111 may be attached to the specimen 13 to facilitate electrical contact. The specimen 13 and the specimen support 101 are preferably coated with an inert masking agent to form a protective coating layer 112 having an opening 113 for exposing the surface area of the specimen 13 to be examined. As shown in FIGS. 3a through 3d, the size and shape of the specimen support 101 may be varied to accommodate the particular size and shape of the specimen to be analyzed.

Figure 4:
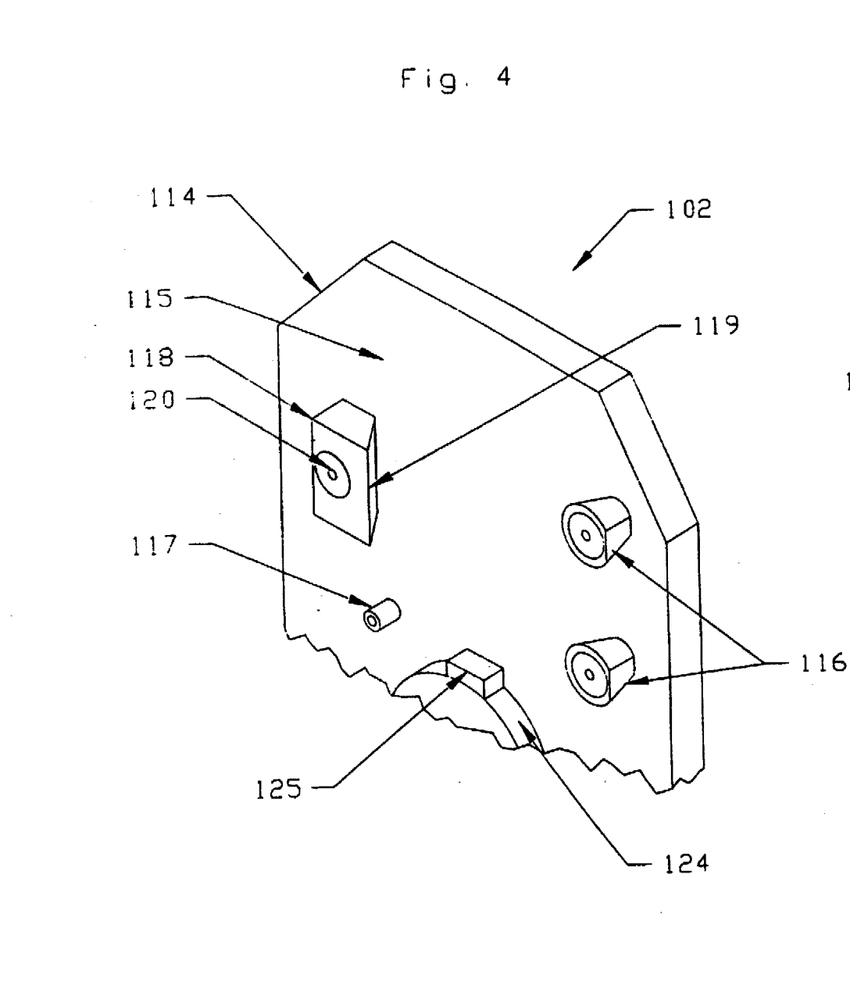
FIG. 4 is a partial perspective view of the rotatable mounting and aligning fixture of the present invention.
Figure 5:
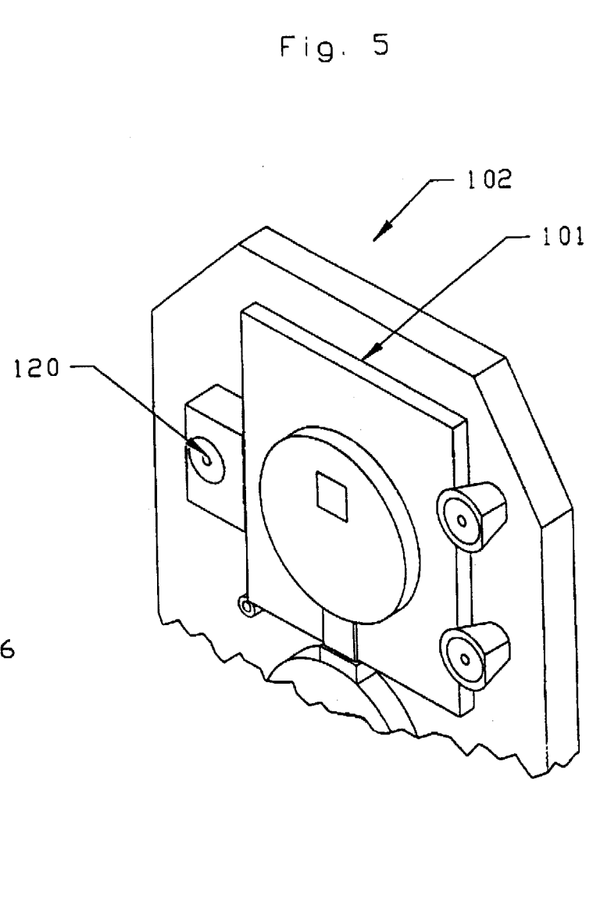
FIG. 5 is a partial perspective view of the rotatable mounting and aligning fixture of the present invention showing the specimen supporting structure mounted thereon.

Referring to FIGS. 2, 4 and 5, the rotatable mounting and aligning fixture 102 comprises a mounting disc or plate 114 having a planar surface 115, and conical positioning retainers 116 and a stop 117 arranged for the precise alignment of the specimen support 101 on the mounting disk 114. The rotatable mounting and aligning fixture 102 further comprises a retaining clamp 118 having a tongue 119 and a set screw 120 for locking the specimen support 101 in position and to assure a rigid engagement between the specimen support 101 and the rotatable mounting and aligning fixture 102. A bore 121 extends through the mounting disc 114 for receiving one end of the drive shaft 103 having a liquid tight end cap 124 and electrical contacts 125. The other end of the drive shaft 103 is rotatably mounted within the conventional motor driven positioning system 104. If the surface layer removal is performed utilizing electrochemical processes, the metal strip 111 (FIGS. 3a through 3d) will contact the electrical contacts 125 which are electrically connected to the positive terminal of a direct current electrical power supply (not shown) by wires (not shown) fed through the hollow drive shaft 103.

Referring to FIG. 2, the positioning system 104 includes a motor driven rotary table 126, such as sold by Velmex, Inc. of Bloomfield, N.Y., secured to a frame 127 for mounting to a motorized slide assembly 128, such as sold by Velmex, Inc., Bloomfield, N.Y., for incremental control of the rotation and the linear position of the rotatable mounting and aligning fixture 102. A proximity sensor 129 and the linear control of the slide assembly 128, and the rotation control of the rotary table 126, cooperate with the electronic controller 108 (FIG. 1) to control the positioning system 104 to precisely align the position of the specimen 13 with respect to the X-ray source 11 of the X-ray diffraction system 10 (FIG. 1).

Figure 6:
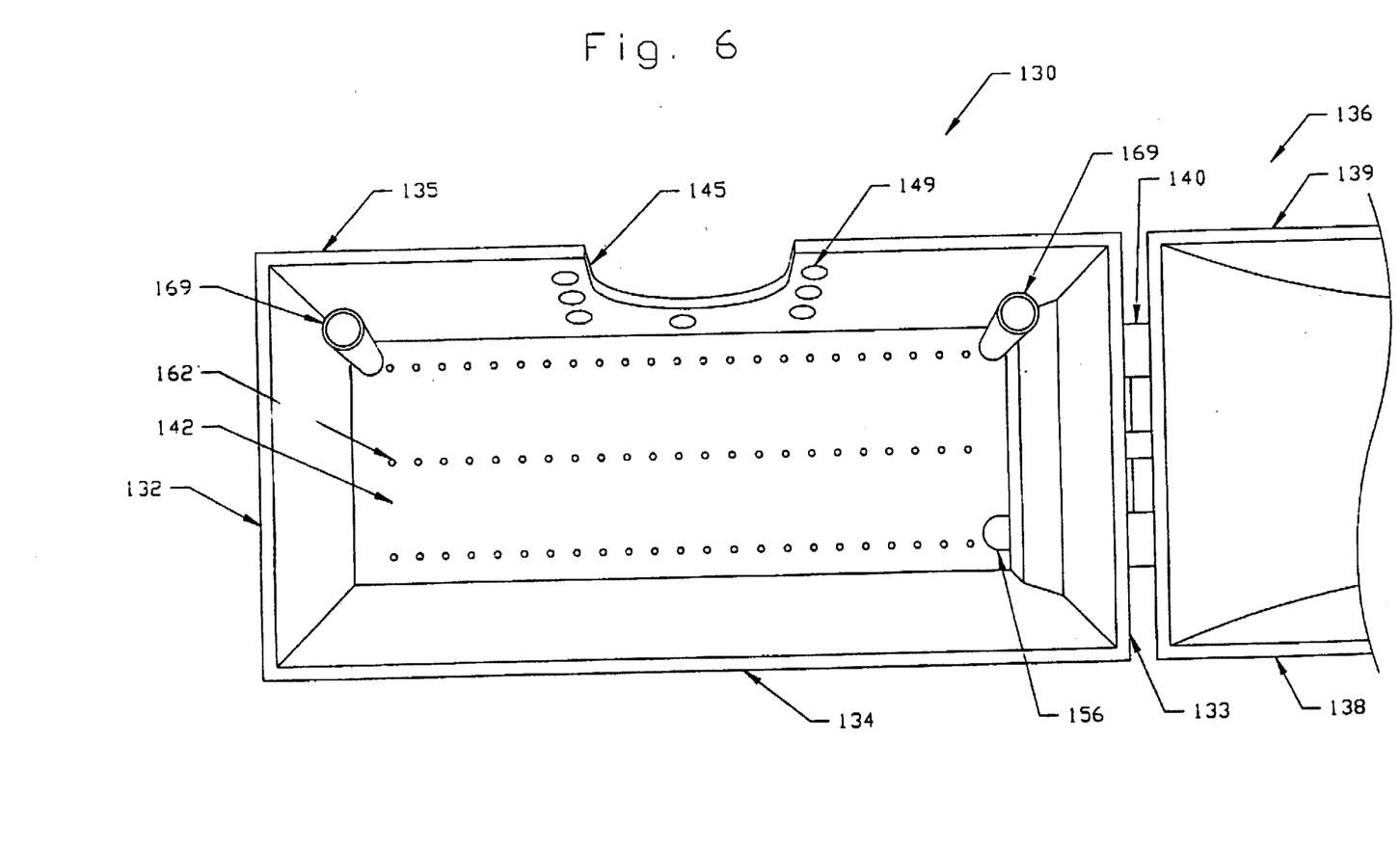
FIG. 6 is a top view of the first half section of the chemical holding tank of the present invention.

The chemical holding tank 105 of the present invention is formed of a material, typically plastic such as polypropylene, which does not react with the particular chemical solution contained in the tank for removing surface material from the specimen to be analyzed. Referring to FIGS. 1, 2, and 6, the chemical holding tank 105 is a two-piece split design comprising a first half section 130 formed by a bottom wall 131, side walls 132, 133 and front and back walls 134, 135 integrally combined in a liquid-tight manner. A second half section 136 formed of a top plate 137 of semi-circular cross section having side walls 138, 139 is pivotally connected to the first half section 130 by a hinge 140. A transparent window 141 is provided such that when the second half section 136 is rotated to a closed position, as shown in FIGS. 1 and 2, the beam of X-rays 12 may be projected from the X-ray source 11 through the transparent window 141 to the surface of the specimen 13 to be analyzed and to permit diffracted radiation to extend and expand outwardly from the surface of the specimen 13 back through the transparent window 141 to be detected by at least one detector 14 positioned at a predetermined position around the specimen 13.

Referring to FIGS. 2 and 6, the first half section 130 includes a recessed bottom panel 142 forming an upper chemical holding chamber 143 and a lower chamber 144. A U-shaped notch 145 extends radially downwardly from the top side edge of the back wall 135 for receiving the drive shaft 103 supporting the rotatable mounting and aligning fixture 102 within the chemical holding tank 105. A plate 146 and a seal 147 each having a bore for receiving the drive shaft 103, and a plurality of evenly spaced apertures 148 which cooperate with a plurality of corresponding apertures 149 in the back wall 135 of the chemical holding tank 105 to receive screws or the like (not shown) to form a liquid tight seal around the drive shaft 103 to prevent fluid leakage from the chemical holding tank 105. The front wall 134 may be provided with outwardly extending brushes 150 (as shown in FIG. 2) for effectively wiping any debris and film from the surface of the specimen being rotated into position for X-ray diffraction measurement.

Figure 7:
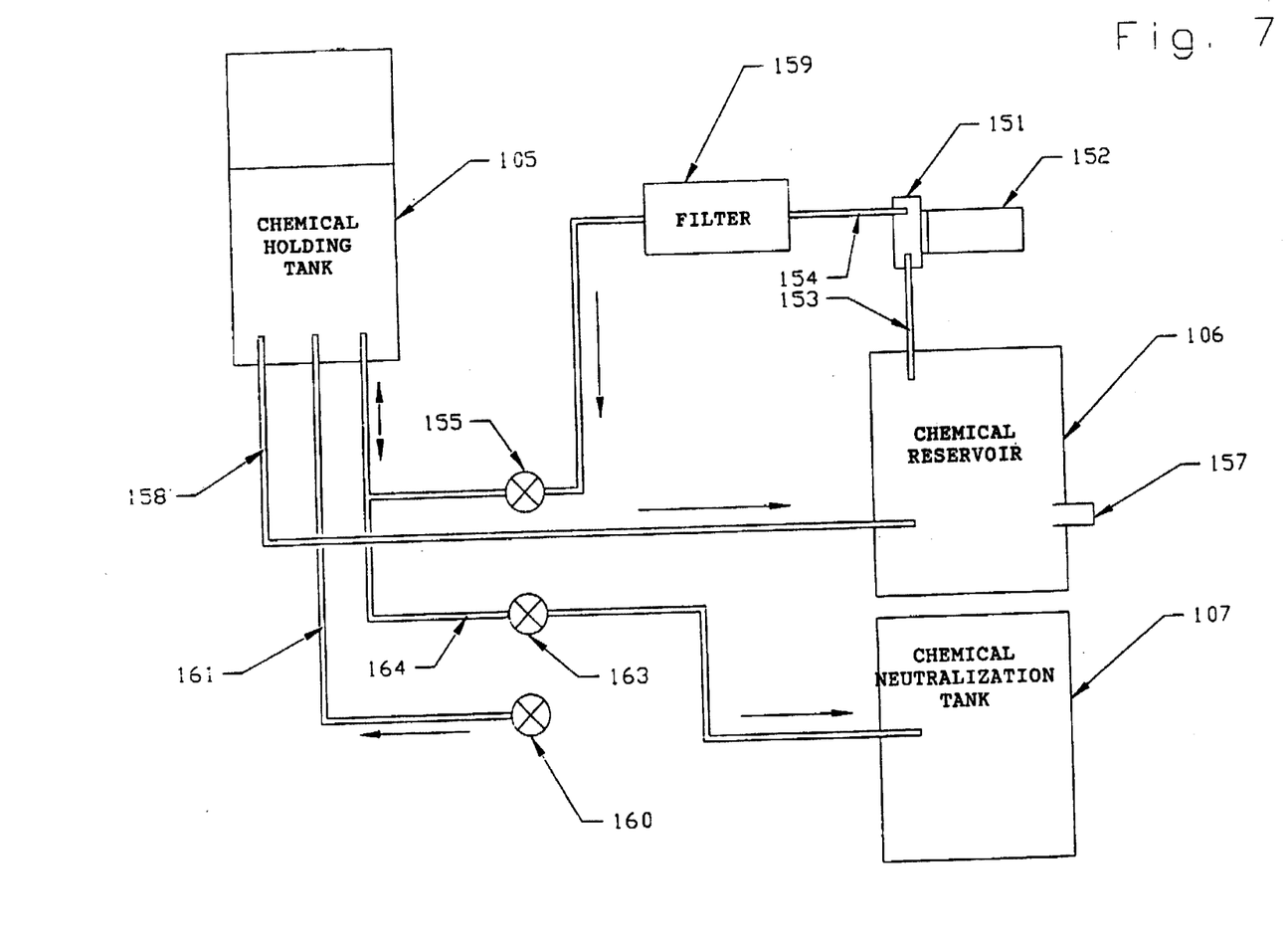
FIG. 7 is a diagram of the closed loop system for the chemical solution of the present invention.

Referring to FIGS. 2 and 7, a chemical solution effective for removing surface material from the specimen is supplied to the upper chemical holding chamber 143 of the chemical holding tank 105 from the chemical solution reservoir 106 through a recirculating closed loop system utilizing a pump 151 driven by an electric motor 152. The pump 151 has an inlet for receiving chemical solution from the chemical solution reservoir 106 through a flexible conduit 153, and an outlet connected to one end of a flexible conduit 154 for receiving discharged chemical solution. The other end of the flexible conduit 154 passes through a filter 159 and then enters into the upper chamber 143 of the chemical holding tank 105 through a valve 155 and an aperture 156 (FIG. 6) in the recessed bottom panel 142. Overflow outlets 169 (FIG. 6) are provided which automatically drain chemical solution from the chemical holding tank 105 when it rises to the level of the overflow opening. The overflowing chemical solution drains into a discharge conduit 158 which empties into the chemical solution reservoir 106. The chemical solution is therefore continuously recirculated, that is, it is withdrawn from the chemical solution reservoir 106, is directed to the chemical holding tank 105 for removing a predetermined amount of surface material from the specimen 13, and returns to the chemical solution reservoir 106. In addition, the negative pressure induced in the discharge conduit 158 by the pump 151 operates as a vacuum vent for drawing vapor out of the chemical holding tank 105 and into the chemical solution reservoir 106 from which it is discharged through outlet 157.

The lower chamber 144 of the chemical holding tank 105 is adapted to receive clean rinse water from a conventional source (not shown) through a valve 160 and a flexible conduit 161. As shown in FIGS. 2 and 6, the recessed bottom panel 142 is provided with a plurality of apertures 162 for providing fluid communication between the lower chamber 144 and the upper chemical holding chamber 143 of the chemical holding tank 105. A second valve 163 and a flexible conduit 164 is provided to drain the rinse water from the chemical holding tank 105 to the chemical neutralization tank 107 for later disposal. In a preferred embodiment of the invention, the chemical neutralization tank 107 can be provided with a conventional liquid filter (not shown) for direct discharge of the rinse water.

In operation of the automated system for the determination of subsurface material properties by X-ray diffraction of the present invention, chemical solution is supplied to the upper chamber of the chemical holding tank from the chemical solution reservoir. If, for example, two specimens are mounted on the rotatable mounting and aligning fixture, one specimen is positioned such that the X-ray beam enters and is diffracted through the transparent window of the second half section while the other specimen is in the chemical bath for removal of a predetermined amount of surface material. The rotatable mounting and aligning fixture is incrementally rotated by rotating the drive shaft of the motor driven positioning system to cycle the specimen(s) between the position for X-ray diffraction measurement and the chemical bath for surface material removal.

The cyclic time is dependent on the rate of material removal and the thickness of each layer to be removed and is programmably controlled by the electronic controller. Typically, the rate of surface layer removal for a particular material, by either a passive or electrolytic process, is determined experimentally. Accordingly, material removal using a chemical bath continues for a predetermined time to attain the desired surface layer. Electrolytic material removal, however, is typically controlled by the electronic controller which monitors and controls the applied current and adjusts the power supply to maintain the current at a constant level to achieve a uniform material removal rate.

After the specimen is rotated from the chemical bath into position for X-ray measurement, the thickness of surface material removed is automatically and precisely determined such as by electronic, mechanical or optical means. Using the slide assembly of the positioning system, the rotatable mounting and aligning fixture is linearly moved until the proximity sensor indicates that the new surface layer of the specimen lies in the same predetermined plane as the original surface layer of the specimen. The linear distance traveled by the rotatable mounting and aligning fixture is then recorded and represents the thickness of the surface removed. When subsurface measurement is complete, the chemical holding tank is drained of the chemical solution and is rinsed with clean water. The plurality of apertures spaced along the recessed bottom panel of the chemical holding tank produce a spray which is effective for removing any chemical residue from the specimen and the rotatable mounting and aligning fixture.

It should be apparent to one skilled in the art that direct measurement of material removal may not be necessary for all studies. Accordingly, in order to reduce the time necessary to conduct the study, certain surface layers are chosen, based on the properties of the material and the objective of the study, for X-ray diffraction measurement. The specimens to be measured are cycled between the chemical bath and the X-ray measurement location. The cycle time is preset based on time calculated for the specimen to be in the chemical bath in order to achieve the desired surface removal. After the final X-ray measurement has been taken, the final thickness of the specimen is measured.

It should be apparent to one skilled in the art that the shape and size of the rotatable mounting and aligning fixture and the corresponding chemical holding tank can vary by convenience. Suitable shapes include, for example, those having circular cross-sections, square cross-sections, and various rectangular cross-sections. It should also be apparent to one skilled in the art that the shape, size and number of specimens can vary by convenience and are limited only by the size of the rotatable mounting and aligning fixture and the chemical holding tank utilized.

Figure 8:
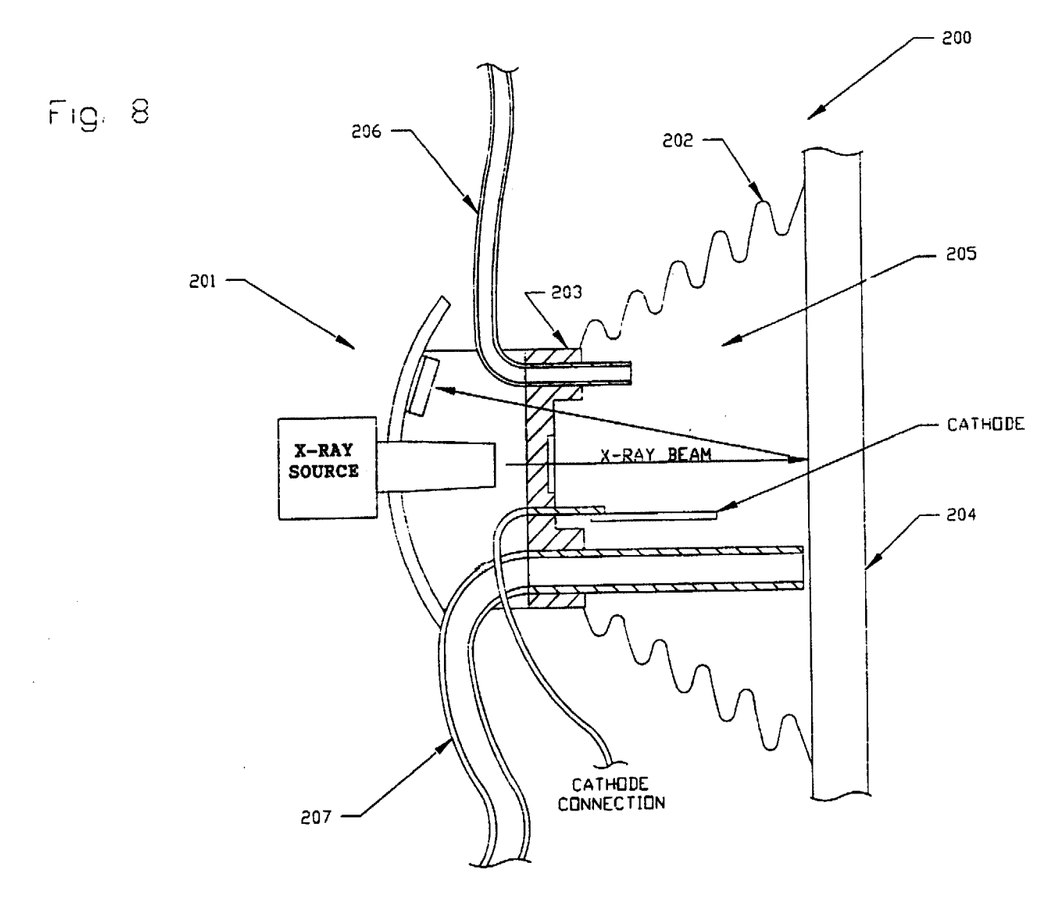
FIG. 8 is a side elevation view of a second embodiment of the invention for use with a portable diffractometer system.

Referring to FIG. 8, another embodiment of the automated system 200 for the determination of subsurface material properties by X-ray diffraction of the present invention is shown for use with a portable diffractometer system 201. The automated system 200 comprises a flexible seal 202 which is attached at one end to the front of a conventional integrated X-ray source 203 and at the other end to the specimen 204 to be analyzed using a clamp, adhesive, or other like means (not shown), to form a chemical holding chamber 205. A chemical solution effective for removing surface material from the specimen 204 is supplied to the chemical holding chamber 205 from a chemical reservoir (previously described) through a recirculating closed loop system utilizing a pump driven by an electric motor. The pump receives chemical solution from the chemical solution reservoir and discharges the chemical solution to a flexible conduit 206 for delivery into the chemical holding chamber 205. After surface layer removal, the chemical solution is drained out of the chemical holding chamber 205 and is recirculated back to the chemical reservoir through a flexible conduit 207. The flow of chemical solution into and out of the chemical holding chamber 205 is electronically controlled by a programmable controller or computer.

There has thus been provided a novel automated system for the determination of subsurface material properties by X-Ray diffraction. Such automated system for the determination of subsurface properties by X-ray diffraction eliminates the need to manually remove a specimen from a diffraction apparatus for surface layer removal and to manually reinsert the specimen into position on the diffraction apparatus for additional X-ray measurements, significantly reduces the time required to perform X-ray diffraction studies, is significantly less labor-intensive than prior art techniques, is significantly less expensive for use in exhaustive studies or high volume or quality control testing, makes the handling of large number of samples less difficult, and significantly reduces the possibility of human error.

Although this invention has been shown and described with respect to detailed embodiments thereof, it will be understood by those skilled in the art that various changes in form and detail thereof may be made without departing from the spirit and scope of the claimed invention.

What is claimed is:

1. An automated system for use with an X-ray diffraction system having an X-ray source for directing a beam of X-rays to the surface of a specimen and a detector for detecting diffracted radiation extending and expanding outwardly from the surface of the specimen, the automated system comprising:
    means for exposing the surface of the specimen to a chemical solution, for a predetermined period of time, to remove a predetermined amount of material from the surface of the specimen;
    means for exposing the specimen, for a predetermined period of time, to a beam of X-rays; and
    means for automatically cycling the specimen between said means for exposing the surface of the specimen to a chemical solution and said means for exposing the specimen to a beam of X-rays.

2. The automated system of claim 1 further comprising means for rinsing the specimen.

3. The automated system of claim 1 further comprising means for controlling the position of the specimen with respect to the X-ray source.

4. The automated system of claim 1 further comprising means for supplying a steady supply of chemical solution to the surface of the specimen.

5. The automated system of claim 1 further comprising means for measuring the amount of material removed from the surface of the specimen.

6. An automated system for use with an X-ray diffraction system having an X-ray source for directing a beam of X-rays to the surface of a specimen and a detector for detecting diffracted radiation extending and expanding outwardly from the surface of the specimen, the automated system comprising:
    a chemical holding tank having a chamber for holding a supply of chemical solution for removing material from the surface of the specimen; and
    a rotatable mounting and aligning fixture for rotating the specimen into said chamber for surface material removal and for rotating the specimen out of said chamber and into a position to receive a beam of X-rays from the X-ray source.

7. The automated system of claim 6 further comprising an electronic controller for controlling the cycling of the specimen between said chamber and into position to receive a beam of X-rays from the X-ray source.

8. The automated system of claim 6 further comprising a specimen support for mounting and supporting the specimen on said rotatable mounting and aligning fixture.

9. The automated system of claim 8 wherein said specimen support is formed of an inert material.

10. The automated system of claim 8 wherein said specimen support is formed of glass.

11. The automated system of claim 8 wherein said specimen support includes a metal strip for providing an electrical contact with the specimen.

12. The automated system of claim 11 wherein said rotatable mounting and aligning fixture further comprises a contact for electrically contacting said metal strip, wherein said contact is electrically connected to the positive terminal of an electrical power source.

13. The automated system of claim 8 wherein said specimen support comprises means for securing a specimen into a precisely aligned position on said rotatable mounting and aligning fixture.

14. The automated system of claim 6 further comprising a motor driven positioning system for incremental control of the rotation and the linear position of said rotatable mounting and aligning fixture.

15. The automated system of claim 14 further comprising an electrical control means for controlling said motor driven positioning system.

16. The automated system of claim 6 further comprising a chemical reservoir for providing a steady supply of said chemical solution to said chamber.

17. The automated system of claim 16 further comprising a pump for continuously circulating said chemical solution between said chamber and said chemical reservoir.

18. The automated system claim 14 wherein said rotatable mounting and aligning fixture comprises a substrate having a planer surface, means for positioning the specimen on said substrate, and means for mounting said rotatable mounting and aligning fixture on said motor driven positioning system.

19. The automated system of claim 18 wherein said substrate is formed of an inert material.

20. The automated system of claim 18 wherein said substrate is formed of glass.

21. An automated system for use with an X-ray diffraction system having an X-ray source for directing a beam of X-rays to the surface of a specimen and a detector for detecting diffracted radiation extending and expanding outwardly from the surface of the specimen, the automated system comprising:

- a chemical holding tank having a chamber for receiving and holding a supply of chemical solution;
- a positioning system for rotating the specimen into said chamber for surface material removal and for rotating the specimen out of said chamber and into position to receive a beam of X-rays from the X-ray source;
- a rotatable mounting and aligning fixture for mounting the specimen onto said positioning system;
- a chemical reservoir for providing the chemical solution to said chamber;
- a pump for delivering chemical solution from the chemical reservoir to said chamber; and
- electronic means for controlling the cyclic rotation of said positioning system.

22. The automated system of claim 21 further comprising electronic means for controlling the rotation and the linear position of the specimen.

23. The automated system of claim 21 further comprising means for rinsing the specimen.

24. The automated system of claim 21 further comprising means for venting vapor out of said chemical holding tank.

25. An automated system for use with an X-ray diffraction system having an integrated X-ray source for directing a beam of X-rays to the surface of a specimen and a detector for detecting diffracted radiation extending and expanding outwardly from the surface of the specimen, the automated system comprising:

- a flexible seal having one end attached to the integrated X-ray source and the other end to the specimen to form a chemical holding chamber; and
- means for circulating a chemical solution in and out of said chemical holding chamber.

26. The automated system of claim 25 further comprising a chemical reservoir for supply chemical solution to said chemical holding chamber.

27. The automated system of claim 25 further comprising electronic control means for controlling the flow of chemical solution into and out of said chemical holding chamber.

28. The automated system of claim 25 further comprising means for venting vapor from said chemical holding chamber.

* * * * *